United States Patent [19]

Hagiwara et al.

[11] Patent Number: 5,269,308
[45] Date of Patent: Dec. 14, 1993

[54] ULTRASONIC DOPPLER IMAGING APPARATUS

[75] Inventors: Hisashi Hagiwara, Yokohama; Hiroshi Fukukita, Tokyo; Morio Nishigaki, Fujisawa, all of Japan

[73] Assignee: Matsushita Electric Industrial Co., Ltd., Osaka, Japan

[21] Appl. No.: 912,752

[22] Filed: Jul. 13, 1992

[30] Foreign Application Priority Data

Jul. 25, 1991 [JP] Japan .................. 03-186067
Aug. 1, 1991 [JP] Japan .................. 03-193106

[51] Int. Cl.⁵ .............................................. A61B 8/06
[52] U.S. Cl. .................. 128/661.09; 73/861.25
[58] Field of Search ............... 128/661.08, 661.09, 128/660.05, 662.06; 73/861.25

[56] References Cited

U.S. PATENT DOCUMENTS 4,541,437  9/1985  Amemiya ............... 128/661.09
4,848,354  7/1989  Angelsen et al. .......... 128/660.05

FOREIGN PATENT DOCUMENTS

6359938  3/1988  Japan .

Primary Examiner—William E. Kamm
Assistant Examiner—George Manuel
Attorney, Agent, or Firm—Stevens, Davis, Miller & Mosher

[57] ABSTRACT

Disclosed is an ultrasonic Doppler imaging apparatus in which the velocity of a blood flow in a living body can be computed with high precision without increasing a scale of a signal processing circuit, so that a Doppler color image having satisfactory image quality is displayed. In the apparatus, an ultrasonic pulse signal is transmitted into the living body and is reflected from a target in the living body to be received by an ultrasonic probe, and the reception signal is subjected to quadrature phase detection to obtain an I signal and a Q signal. When an amplitude evaluating unit evaluates on the basis of the intensity of the I and Q signals that the reception signal contains many clutter components, a cut-off frequency of high-pass filters is increased by the application of a control signal (A) to thereby eliminate low-frequency clutter components. The outputs of the high-pass filters are converted into blood flow velocity information to be displayed as a Doppler color image.

6 Claims, 10 Drawing Sheets

INPUT POWER COMPUTING SECTION 110, OUTPUT POWER COMPUTING SECTION 111

GATE SIGNAL 124

CLEAR SIGNAL 126

FIG. 8

FROM INPUT POWER COMPUTING SECTION 110

FROM OUTPUT POWER COMPUTING SECTION 111

ULTRASONIC DOPPLER IMAGING APPARATUS

BACKGROUND OF THE INVENTION

This invention relates to an ultrasonic Doppler imaging apparatus for use in ultrasonic diagnosis in the medical diagnosis so as to make real time measurement of a velocity of blood flow in a living body.

An ultrasonic Doppler imaging apparatus for the medical diagnosis is already known, in which the technique of ultrasonic pulse Doppler measurement and the technique of pulse reflection are used in combination so as to obtain both information of a blood flow and information of a tomographic image (a B-mode image) in a living body by the use of an ultrasonic probe and then to display a real time color image of the blood flow information superposed on the tomographic image. An ultrasonic diagnostic apparatus disclosed in JP-A-63-59938 is an example of such an ultrasonic Doppler imaging apparatus.

A conventional ultrasonic Doppler imaging apparatus will now be described hereunder before describing the present invention.

Figure 1:
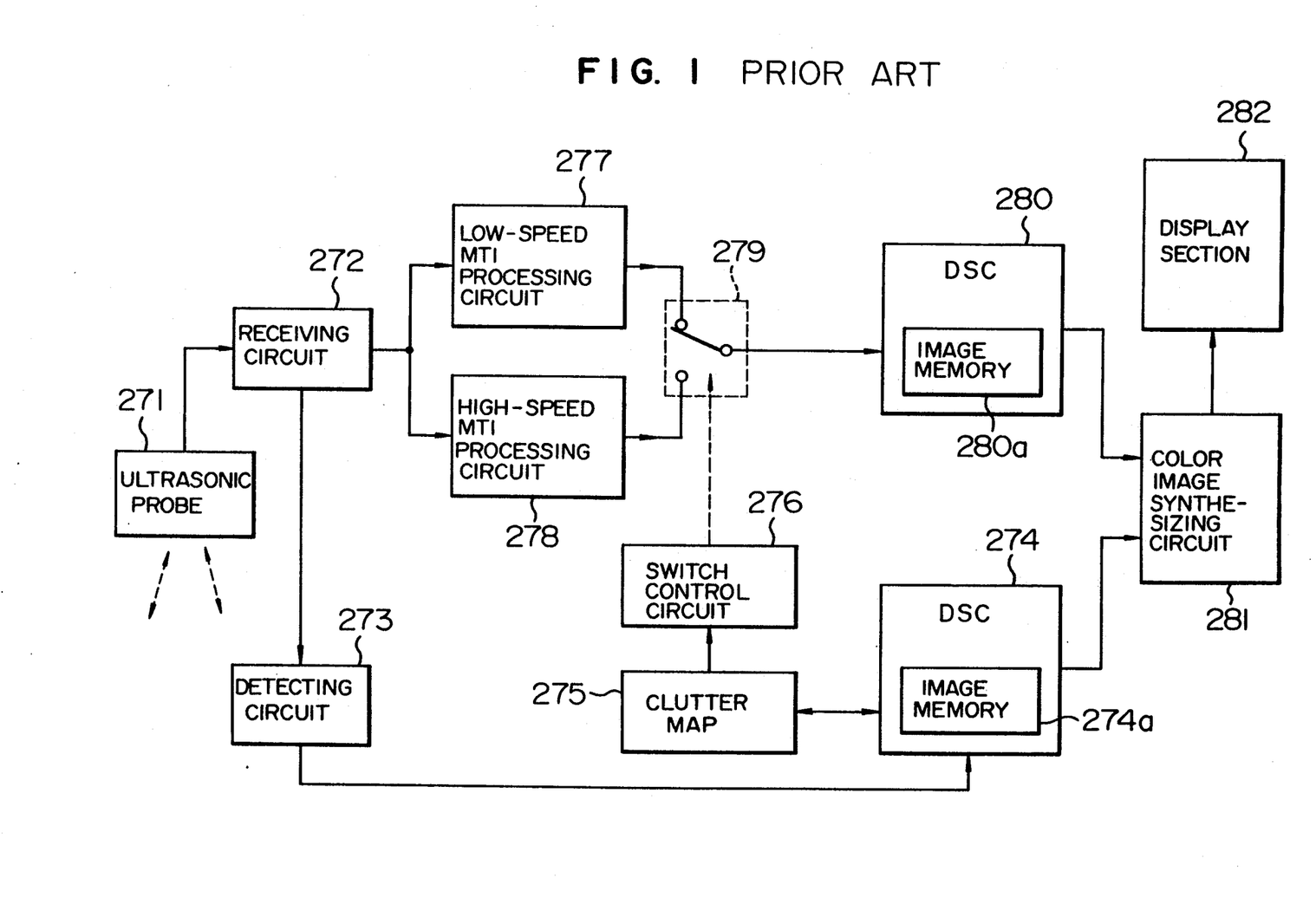
FIG. 1 is a block diagram showing the structure of a conventional ultrasonic Doppler imaging apparatus.

FIG. 1 shows the structure of a conventional ultrasonic Doppler imaging apparatus. Referring to FIG. 1, ultrasonic waves reflected from a body under test is received by an ultrasonic probe 271 and is then amplified through a receiving circuit 272. This received signal includes both a wave component reflected from a stationary part of the body under test and a wave component reflected from a moving part of the body under test. An output signal of the receiving circuit 272 is supplied in parallel with a first and a second signal processing system.

In the first signal processing system, the output signal of the receiving circuit 272 is amplified and detected through a detecting circuit 273 to provide a B-mode signal, and then this B-mode signal is converted in a DSC (digital scan converter) 274 to a digital signal, which is stored in an image memory 274a contained in the DSC 274. A clutter decision level is set beforehand in a clutter map 275, and the level of each signal stored in the image memory 274a is compared with the clutter decision level. When the level of each of the stored signals exceeds the clutter decision level, an address of that signal is recorded, so that a map showing positions, where the clutters exist, is prepared.

In the second signal processing system, the output signal of the receiving circuit 272 is applied to each of two MTI (moving target indicator) processing circuits 277 and 278. One of the two MTI processing circuits, that is, the low-speed MTI processing circuit 277, generates its output signal without eliminating reflected waves coming from a slowly moving target. Therefore, when the clutter signals exist in an input signal to the low-speed MTI processing circuit 277, an output signal from the low-speed MTI processing circuit 277 is generated without sufficiently eliminating the clutter signals.

The other high-speed MTI processing circuit 278 generates an output signal, in which reflected waves coming from a moving target, whose position does not change appreciably, are eliminated, so that the clutter signals contained therein are also completely eliminated. Therefore, where the clutter signal does not exist, reflected waves coming from a slowly moving target are eliminated. These two MTI processing circuits 277 and 278 are switched over by a switch 279 controlled by a switch control circuit 276. An output signal of the receiving circuit 272 is usually processed by the low-speed MTI processing circuit 277 to display a color image of a moving target. However, when a sound ray is incident on a position where the clutter signal exists, that is, when a clutter address signal in the clutter map 275 coincides with a digitized B-mode signal stored at an address of the image memory 274a in the DSC 274, an output signal of the clutter map 275 is applied to the switch control circuit 276, so that the switch 279 is changed over to the side of the high-speed MTI processing circuit 278. Then, the output signal of the receiving circuit 272 is processed by the high-speed MTI processing circuit 278, and the output signal of this MTI processing circuit 278 is applied to the DSC 280.

In the manner described above, the existing positions of the clutter signals are recorded on the clutter map 275. Whenever the existence of the clutter signal is detected, the switch 279 is changed over to successively store the output signal of the high-speed MTI processing circuit 278 in an image memory 280a in the DSC 280. Then, the contents of the image memory 280a are read out and supplied to a color image synthesizing circuit 281 to be synthesized into a color image, and the synthesized color image is displayed on a display section 282.

However, the conventional ultrasonic Doppler imaging apparatus has a drawback such that it is necessary for this apparatus to comprise the two MTI processing circuits, that is, the low-speed MTI processing circuit 277 and the high-speed MTI processing circuit 278, thereby resulting in an undesirable increase in the scale of the signal processing circuit.

SUMMARY OF THE INVENTION

It is an object of the present invention to provide an advanced ultrasonic Doppler imaging apparatus which can compute a blood flow velocity of a living body with high precision and yet without increasing the scale of the signal processing circuit and which can produce a good Doppler color image.

Another object of the present invention is to provide an ultrasonic Doppler blood flow meter in which, in response to the frequency distribution of a low frequency signal which is a clutter signal contained in a reception signal reflected from a part of a body under test, the signal cut-off characteristic of filter means for eliminating the low frequency signal can be automatically set to have a suitable value, and therefore a satisfactory blood flow image can be obtained and the operability of the diagnostic apparatus can be improved.

According to one aspect of the present invention, there is provided an ultrasonic Doppler imaging apparatus comprising ultrasonic pulse transmitting and receiving means for transmitting an ultrasonic pulse signal into a body under test and outputting a reception signal received by the reflection of the ultrasonic pulse signal from a scattering portion of the body under test, memory means for storing the reception signals, high-pass filter means to which the reception signals are supplied from, the memory means, amplitude evaluating means for evaluating an amplitude of a group of reception signals originated from the same depth of the body under test by reading out the reception signals stored in the memory means, control means for controlling the high-pass filter means to increase a cut-off frequency of the high-pass filter means so as to eliminate low-frequency clutter components when a result of evaluation by the amplitude evaluating means proves that many clutter components are contained in the reception signals, and velocity computing means for computing the moving velocity of the scattering portion of the body under test on the basis of an output signal of the high-pass filter means.

Further, the amplitude evaluating means of the ultrasonic Doppler imaging apparatus described above is constructed to have low-frequency component eliminating means for eliminating clutter components having very low frequencies.

Further, the high-pass filter means has a fixed delay time, and also has signal passing means so that, when a clutter intensity is low, the reception signals are prevented from passing through the high-pass filter means, and the velocity computing means directly obtains the moving velocity of the scattering portion of the body under test.

According to another aspect of the present invention, there is provided an ultrasonic Doppler blood flow meter comprising means for transmitting an ultrasonic pulse signal into a living body and for receiving an echo signal from a reflecting portion of the living body, phase detection means for subjecting a received echo signal to phase detection, MTI filter means for eliminating a low frequency signal from a phase detection output signal, power computing means for computing a power of an input signal to the filter means and a power of an output signal from the filter means, respectively, power comparing means for comparing the two powers with each other to thereby generate a comparison output signal, target value setting means for setting a target value for the low frequency signal to be eliminated by the MTI filter means, control means for controlling the characteristic of the MTI filter means so that the value of the comparison output signal from the power comparing means becomes equal to the target value set by the target value setting means, and velocity computing means for computing a moving velocity of a reflecting portion of the living body.

The ultrasonic Doppler blood flow meter described above is constructed so that the target value set by the target value setting means can be set by manipulating a control panel.

Thus, according to the first aspect of the present invention, the ultrasonic Doppler imaging apparatus is constructed so that the cut-off frequency of the high-pass filter means is increased thereby to efficiently eliminate low-frequency clutter components, when a result of evaluation of the amplitude of a reception signal received upon transmission of a ultrasonic pulse signal into the living body proves that the reception signal contains many clutter components, and, as a result, the blood flow velocity can be computed with high precision and yet without requiring an enlarged scale of the MTI processing circuit, and a satisfactory Doppler color image can be obtained.

Further, because clutter components having very low frequencies are efficiently eliminated at the time of amplitude evaluation of the reception signal, the blood flow velocity can be computed with high precision and yet without requiring a large scale MTI processing circuit, and a satisfactory Doppler color image can be obtained.

Besides, a delay time of the high-pass filter means may be fixed, and the high-pass filter means may have a signal passing function such that, when the intensity of clutter components is low, the reception signal is not allowed to pass through the high-pass filter means, and the blood flow velocity can be computed directly from the reception signal. The above arrangement enables easy design of the operating timing of the signal processing circuit and also elevates the sensitivity of the apparatus when the blood flow velocity is low, so that the blood flow velocity can be computed with high precision and yet without requiring a large scale MTI processing circuit, and a satisfactory Doppler color image can be obtained.

Moreover, according to the second aspect of the present invention, a power of an input signal and a power of an output signal to and from the filter means, respectively, which filter means eliminates a low frequency signal, that is a clutter signal, from the received echo signal, are computed by the power computing means and then compared with each other in the comparing means, and the coefficient of the filter means is controlled by the control means so that the value of an output signal of the comparing means becomes equal to a target value set by the target value setting means. Thus, in response to the frequency distribution of a low frequency signal, that is a clutter signal, the filter characteristic can be automatically set to a suitable value without requiring to manipulate a control panel.

DESCRIPTION OF THE PREFERRED EMBODIMENTS

Figure 2:
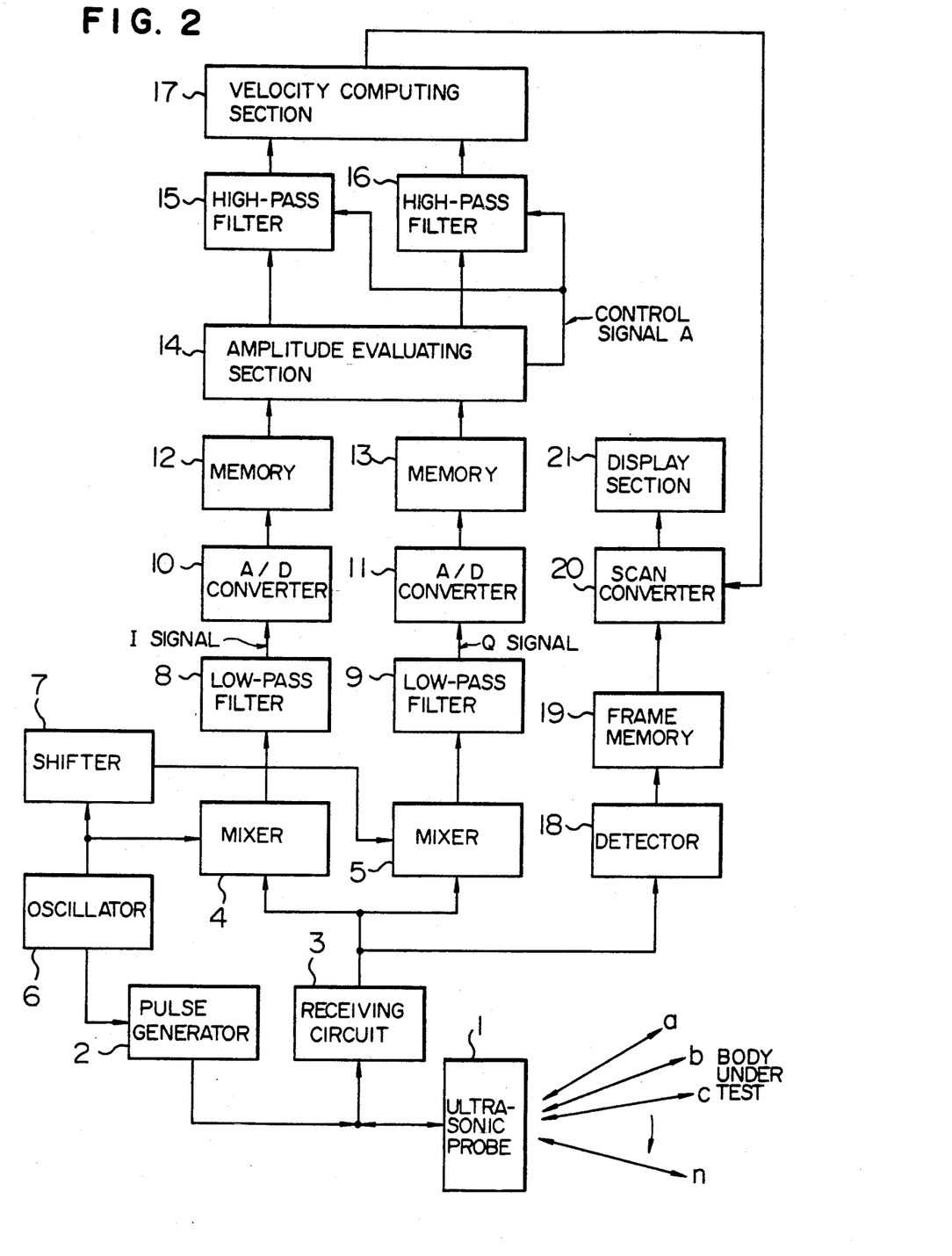
FIG. 2 is a block diagram showing the structure of a first embodiment of the present invention.

FIG. 2 is a block diagram showing the structure of an ultrasonic Doppler imaging apparatus of a first embodiment of the present invention. Referring to FIG. 2, the ultrasonic Doppler imaging apparatus comprises an ultrasonic probe 1, a pulse generator 2, a receiving circuit 3, mixers 4 and 5, an oscillator 6, a phase shifter 7, low-pass filters 8 and 9, A/D convertors 10 and 11, memories 12 and 13, an amplitude evaluating section 14, high-pass filters 15 and 16, a velocity computing section 17, a detector 18, a frame memory 19, a scan convertor 20 and a display section 21.

The amplitude evaluating section 14, the high-pass filters 15,16 and the velocity computing section 17 carry out MTI processing, and a structure and an operation thereof will be described later in detail.

The operation of the ultrasonic Doppler imaging apparatus having the above structure will hereinafter be described.

Referring to FIG. 2, the ultrasonic probe 1 located close to a body under test is driven by the pulse generator 2 to successively radiate ultrasonic pulses in the directions indicated by symbols a, b, c, . . . , n, thereby effecting sector scanning. The ultrasonic pulse is first radiated N times, for example, about eight times, in the direction indicated by symbol a. A signal reflected from a blood flow in the body under test and Doppler-shifted in the first pulse transmission and reception in the direction indicated by the symbol a, is received by the ultrasonic probe 1, and, after having been converted into an electrical signal, the signal is supplied to the receiving circuit 3. A portion of the reception signal from the receiving circuit 3 is supplied to the frame memory 19 through the detector 18, while the other portion of the reception signal is subjected to quadrature phase detection.

In effecting the quadrature phase detection, an output signal of the oscillator 6, which is driven in synchronism with the operation of the pulse generator 2, is applied directly to the mixer 4, and it is also applied to the mixer 5 after its phase is shifted by 90° through the phase shifter 7. The output signals of the mixers 4 and 5 pass through the low-pass filters 8 and 9 to become an I signal and a Q signal respectively.

After the I signal and the Q signal are converted into digital data through the A/D convertors 10 and 11, respectively, the converted digital data are stored in the memories 12 and 13 respectively. Thus, the data received after the ultrasonic pulses have been radiated N times in the direction indicated by symbol a are recorded in the memories 12 and 13.

Then, the data obtained by the reflection of the ultrasonic pulses from the same depth of the body under test are read out as a group from the memories 12 and 13. In this case, the amplitude evaluating section 14 evaluates the amplitude of each of the N memory outputs of the digital data of the I and Q signals, respectively, thereby to produce a control signal A. On the other hand, the I signal and the Q signal, which passed straightly through the amplitude evaluating section 14, are applied to the high-pass filters 15 and 16, respectively, where low-frequency clutter components are eliminated. In this case, a large amplitude of the I and Q signals is assumed to indicate a large amount of clutter components. In such a case, the control signal A is applied to the high-pass filters 15 and 16 to raise a cut-off frequency of each of these high-pass filters 15 and 16. The I and Q signal data, from which clutter components have been eliminated through the high-pass filters 15 and 16, are then converted into velocity information in the velocity computing section 17. A color image signal of this velocity information is written in the scan converter 20 together with B-mode image information supplied from the frame memory 19.

The velocity computation described above is sequentially carried out with respect to each depth in the direction indicated by symbol a. After the velocity computation with respect to all depths in the direction indicated by symbol a is completed, the velocity computation in the directions indicated by symbols b, c, . . . , n is successively carried out to form a Doppler image which is displayed in the form of a Doppler color image on the display section 21.

Thus, when many clutter components are detected in the reception signal, the frequency characteristic of the high-pass filters 15 and 16 can be suitably changed under the control of the control signal A supplied from the amplitude evaluating section 14, so that the velocity of blood flow can be computed with high precision, and a Doppler color image of good quality can be obtained.

Figure 3:
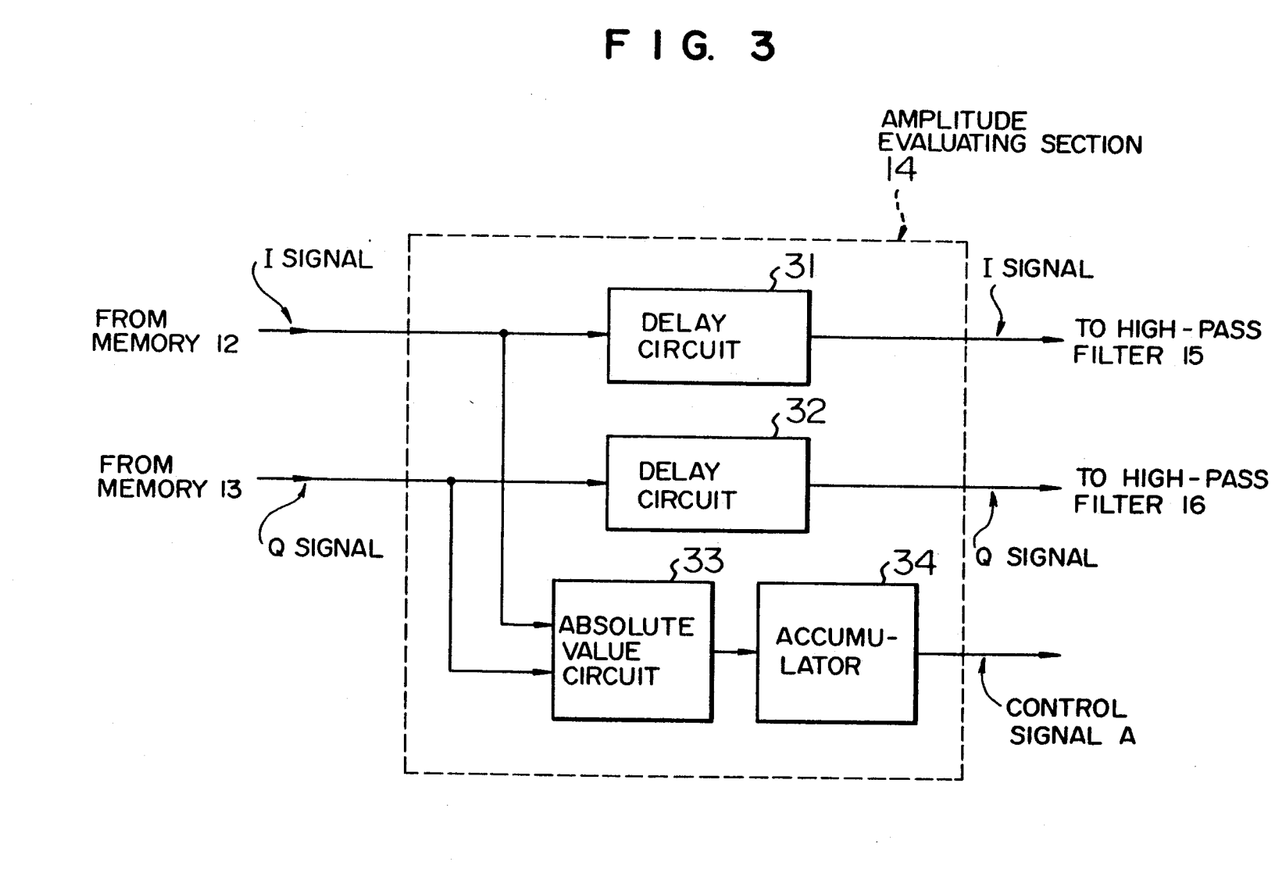
FIG. 3 is a block diagram showing in detail the structure of the amplitude evaluating section in the embodiment shown in FIG. 2.

FIG. 3 shows in detail the structure of the amplitude evaluating section 14. Referring to FIG. 3, the amplitude evaluating section 14 comprises delay circuits 31 and 32, an absolute value circuit 33 and an accumulator 34. The absolute value circuit 33 computes a root-mean-square value of each of the I and Q signal data. The accumulator 34 computes a sum of N root-mean-square values computed by the absolute value circuit 33 to produce the control signal A for controlling the characteristic of the high-pass filters 15 and 16. The delay circuits 31 and 32 operate to delay the I and Q signal data, respectively, so that delayed I and Q signal data are supplied to the high-pass filters 15 and 16, respectively, with the time axis of the output delayed I and Q signal data aligned with that of the control signal A outputted from the accumulator 34.

Thus, the amplitude evaluating section 14 can produce the control signal A for controlling the characteristic of the high-pass filters 15 and 16 in response to the intensity of the reception signal.

Figure 4:
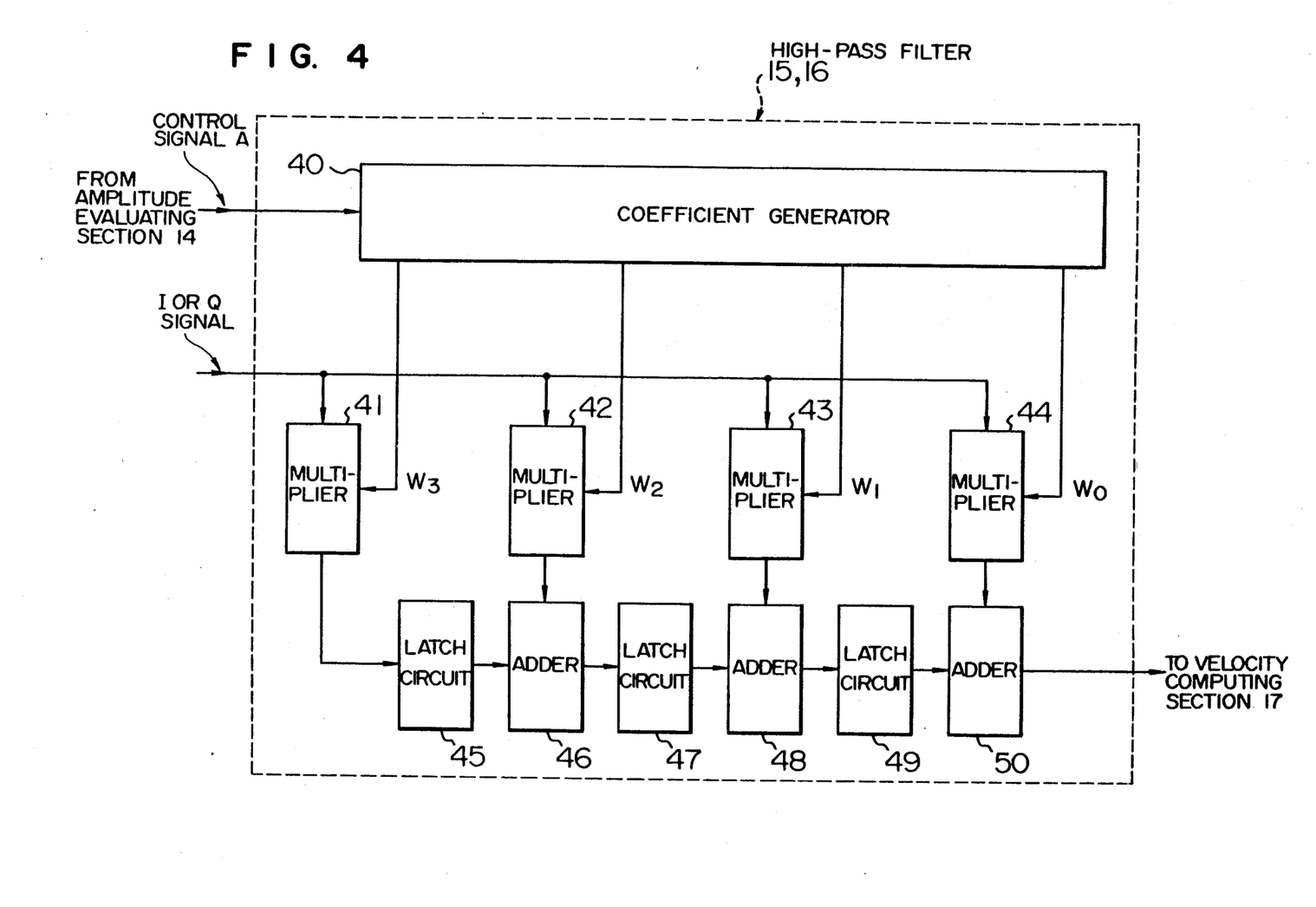
FIG. 4 is a block diagram showing in detail the structure of each of the high-pass filters in the embodiment shown in FIG. 2.

FIG. 4 is a block diagram showing in detail the structure of each of the high-pass filters 15 and 16. Referring to FIG. 4, each of the high-pass filters 15 and 16 comprises a coefficient generator 40, multipliers 41, 42, 43 and 44, latch circuits 45, 47 and 49, and adders 46, 48 and 50.

The coefficient generator 40 generates coefficients $W_0$, $W_1$, $W_2$ and $W_3$ whose values are changed by the value of the control signal A applied to the coefficient generator 40. For example, when the intensity of the reception signal is high, the control signal A controls the coefficient generator 40 to increase the cut-off frequency of the high-pass filters 15 and 16. As a concrete example of the respective values of the coefficients $W_0$, $W_1$, $W_2$ and $W_3$, each of the high-pass filters 15 and 16 operates as a tertiary FIR filter, when $W_0=1$, $W_1=-3$, $W_2=3$ and $W_3=-1$, while, operates as a primary FIR filter, when $W_0=1$, $W_1=-1$, and $W_2=W_3=0$. Also, when $W_0=1$, and $W_1=W_2=W_3=0$, the data are allowed to merely pass through each of the high-pass filters 15 and 16. In the case where the data pass through each of the high-pass filters 15 and 16, the coefficients may be suitably selected ($W_3=0$), so that the data necessarily pass through the latch circuits 45, 47 and 49 and thereby the latency or delay time can be kept constant.

As described above, by making the latency have a constant value in both the high-pass filters 15 and 16, it become possible to facilitate the design of the timing of signal processing. When the intensity of the clutter components is low, by having the high-pass filters 15 and 16 provided with the signal passing function, the blood flow velocity can be computed from the I and Q signal data themselves without making these signal data pas through the high-pass filters 15 and 16, whereby the sensitivity of measurement of a blood flow having low velocity can be elevated.

Figure 5:
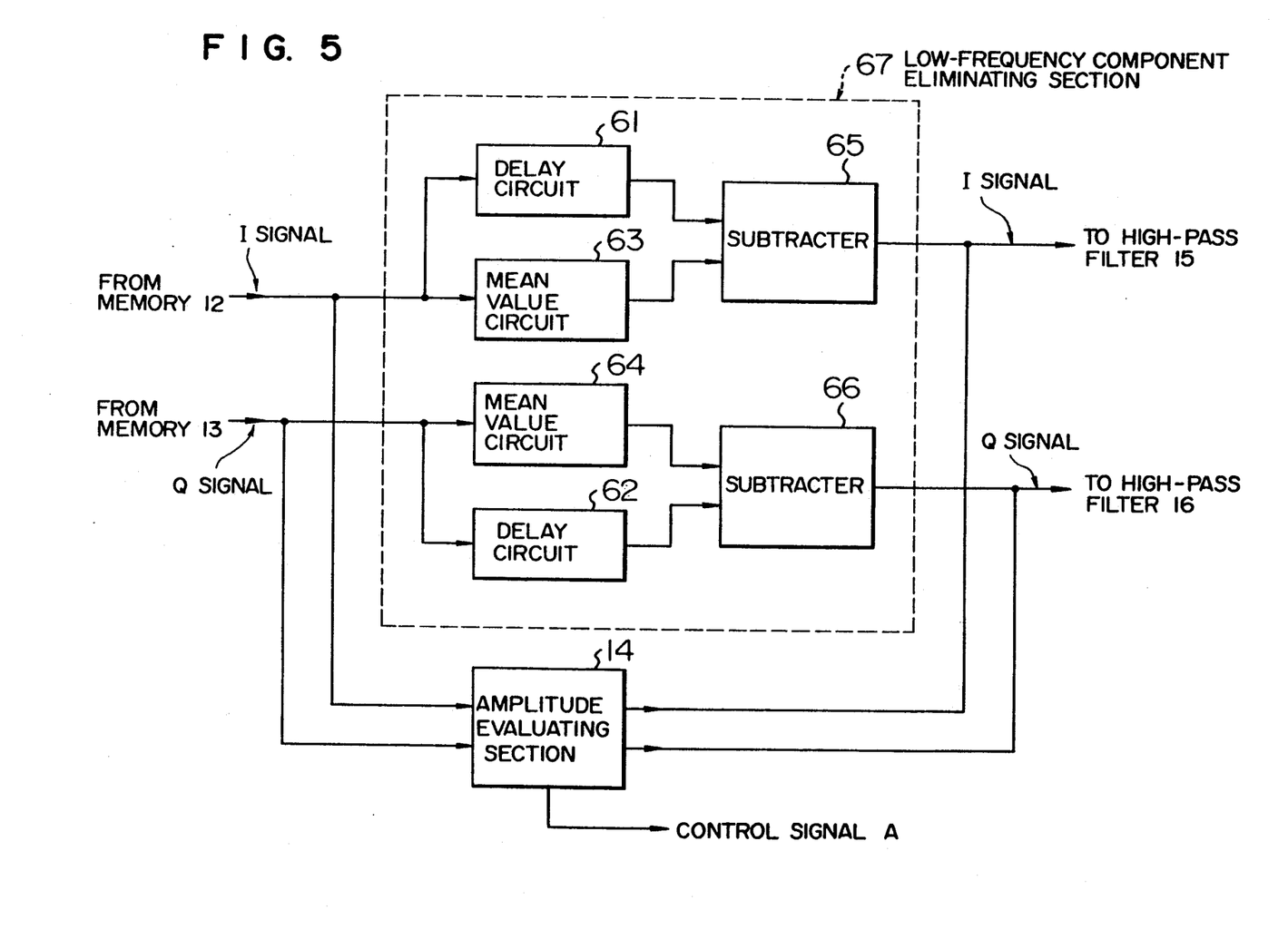
FIG. 5 is a block diagram showing in detail the structure of a low-frequency component eliminating section preferably provided in the embodiment shown in FIG. 2.

FIG. 5 shows the structure of a low-frequency component eliminating section 67 which is a further embodiment section of the present invention and which may be disposed in parallel with the amplitude evaluating section 14. Referring to FIG. 5, the low-frequency component eliminating section 67 comprises delay circuits 61 and 62, mean value circuits 63 and 64, and subtracters 65 and 66. In the case of the I signal data, the mean value circuit 63 computes a mean value of the I signal data of N. After a mean value of the I signal data of N is computed by the mean value circuit 63, this mean value is subtracted in the subtracter 65 from the I signal data which have passed through the delay circuit 61.

By virtue of the foregoing computation, a mean value of the I signal data, that is, a DC component or signal components having very low frequencies can be eliminated. Also, in the case of the Q signal data, signal components having very low frequencies can be eliminated in the same manner.

In the manner described above, clutter components having very low frequencies can be eliminated from the I and Q signal data. The outputs of the delay circuits 31 and 32 in the amplitude evaluating section 14 or the outputs of the subtracters 65 and 66 in the low-frequency component eliminating section 67 are applied to the high-pass filters 15 and 16, respectively. In the case where the low-frequency component eliminating section 67 applies its outputs to the high-pass filters 15 and 16, respectively, the high-pass filters 15 and 16 may be forcedly placed in the signal passing state.

Thus, the low-frequency component eliminating section 67 disposed in parallel with the amplitude evaluating section 14 is useful in eliminating only the clutter components having very low frequencies, so that the sensitivity of the apparatus for a blood flow of low velocity can be elevated.

Figure 6:
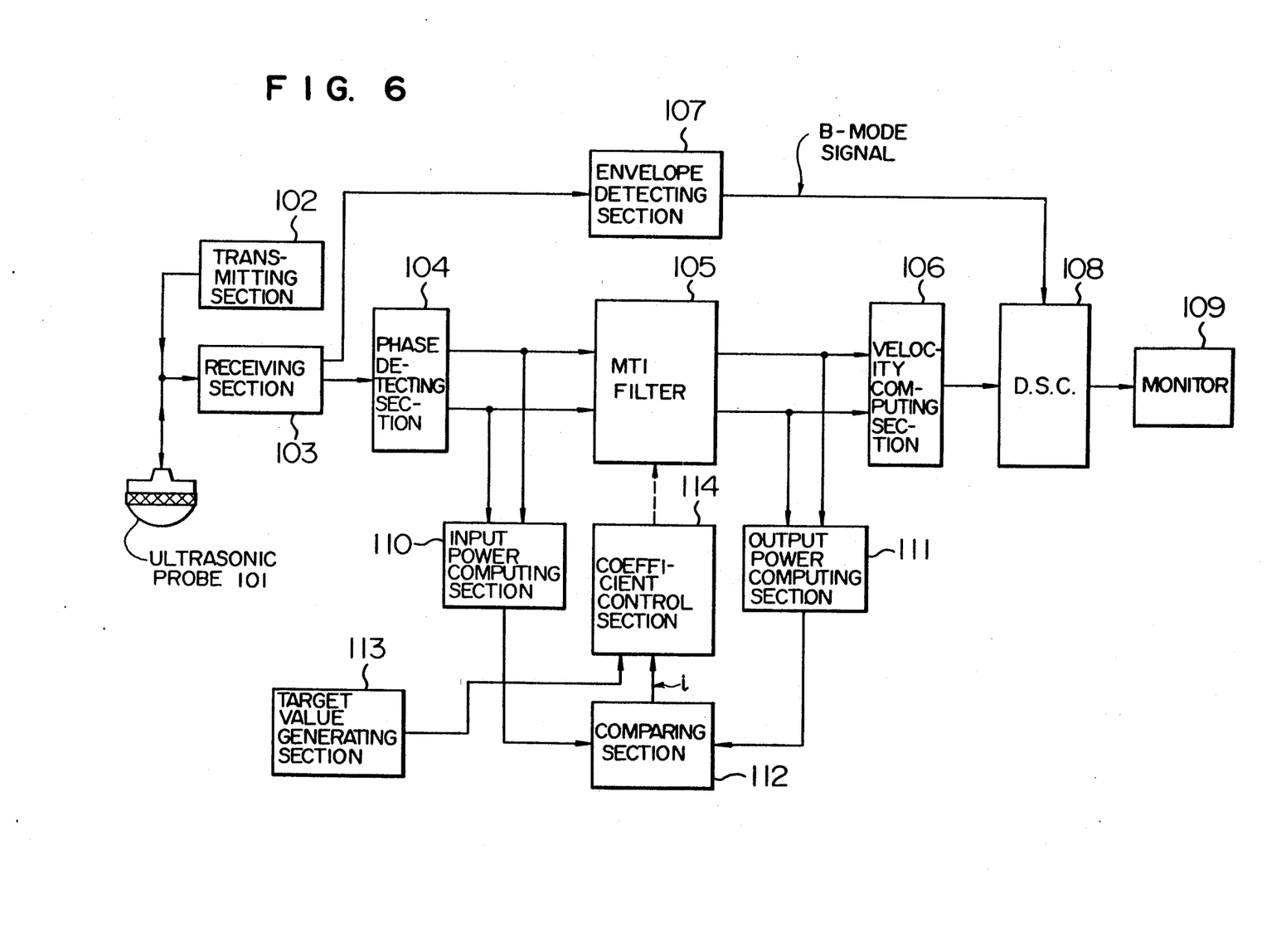
FIG. 6 is a block diagram showing the structure of a second embodiment of the present invention.

FIG. 6 is a block diagram showing the structure of an ultrasonic Doppler blood flow meter of a second embodiment of the present invention. Referring to FIG. 6, the ultrasonic Doppler blood flow meter comprises an ultrasonic probe 101, a transmitting section 102, a receiving section 103, a phase detecting section 104, an MTI filter 105, a velocity computing section 106, an envelope detecting section 107, a digital scan converter (DSC) 108, a monitor 109, input and output power computing sections 110 and 111 respectively, a comparing section 112, a target value generating section 113, and a coefficient control section 114. The ultrasonic probe 101 transmits an ultrasonic pulse signal, which is obtained by converting an electric pulse signal into an ultrasonic pulse signal, into a living body under test, and converts an echo signal, which is received by the reflection of the ultrasonic pulse signal from a blood flow in the living body, into an electric signal. The transmitting section 102 generates an electric pulse signal to be supplied to the ultrasonic probe 101. The receiving section 103 receives and amplifies an electric signal produced by the conversion of the echo signal in the ultrasonic probe 101. An electric signal outputted from the receiving section 103 is subjected to phase detection in the phase detecting section 104. The MTI filter 105 eliminates unnecessary clutter components from an output signal of the phase detecting section 104. The velocity computing section 106 computes the velocity of the blood flow, which has reflected the ultrasonic pulse signal, on the basis of a phase detection output signal which has been outputted from the phase detecting section 104 and from which unnecessary clutter components have been eliminated. An electric output signal from the receiving section 103 is also subjected to envelope detection by the envelope detecting section 107 to produce a B-mode signal. Both a blood-flow velocity signal from the velocity computing section 106 and the B-mode signal from the envelope detecting section 107 are supplied to and mixed together in the digital scan converter (DSC) 108 to be converted into a television signal. A television signal generated by the DSC 108 is displayed on the monitor 109.

The input power computing section 110 computes a power of a phase detection output signal supplied to the MTI filter 105. The output power computing section 111 computes a power of an output signal of the MTI filter 105. The comparing section 112 compares both powers, which have been computed by the respective power computing sections 110 and 111, with each other. The target value generating section 113 sets a target value for the level of the clutter signal to be eliminated by the MTI filter 105, and this target value is preferably set by the manipulation of a control panel. The coefficient control section 114 controls a filter coefficients of the MTI filter 105 so that the value of an output signal of the comparing section 112 becomes equal to the target value set by the target value generating section 113.

The ultrasonic Doppler blood flow meter having the above structure will be described in further detail in conjunction with its operation.

An electric pulse signal generated by the transmitting section 102 is converted into an ultrasonic pulse signal, and it is radiated into a living body under test. A radiated ultrasonic pulse signal is reflected by parts of the living body having different acoustic impedances, such as a tissue and a blood flow, and an echo signal received by the ultrasonic probe 101 is converted into an electric signal there. This electric signal obtained by the conversion of an echo signal is amplified by the receiving section 103, and an output signal of the receiving section 103 is subjected to phase detection by the phase detecting section 104. An output signal of the phase detecting section 104 is supplied to the MTI filter 105, where a low frequency signal, which corresponds to unnecessary clutter components caused by the reflection of the ultrasonic pulse signal from a tissue of a living body, such as a wall of a blood vessel, is eliminated by the function of the MTI filter 105, and an output signal of the MTI filter 105 is supplied to the velocity computing section 106 which computes the velocity of a blood flow. On the other hand, an electric signal which has been obtained provided by the conversion of a received echo signal and which has then been amplified in the receiving section 103, is subjected to envelope detection by the envelope detecting section 107 so as to be converted into a B-mode signal. A blood-flow velocity signal from the velocity computing section 106 and the B-mode signal from the envelope detecting section 107 are mixed together in the digital scan converter (DSC) 108 so as to obtain an appropriate television signal, which is displayed as a two-dimensional blood flow image on the monitor 109. Then, as described already, a power of a phase detection output signal applied to the input to the MTI filter 105 is computed by the input power computing section 110, and a power of an output signal of the MTI filter 105 is computed by the output power computing section 111. These two powers are then compared with each other in the comparing section 112, and a result of the comparison is supplied to the coefficient control section 114. The coefficient control section 114 controls a filter coefficient of the MTI filter 105 so that the value of the output signal of the comparing section 112 becomes equal to a target value set by the target value generating section 113.

Figure 7:
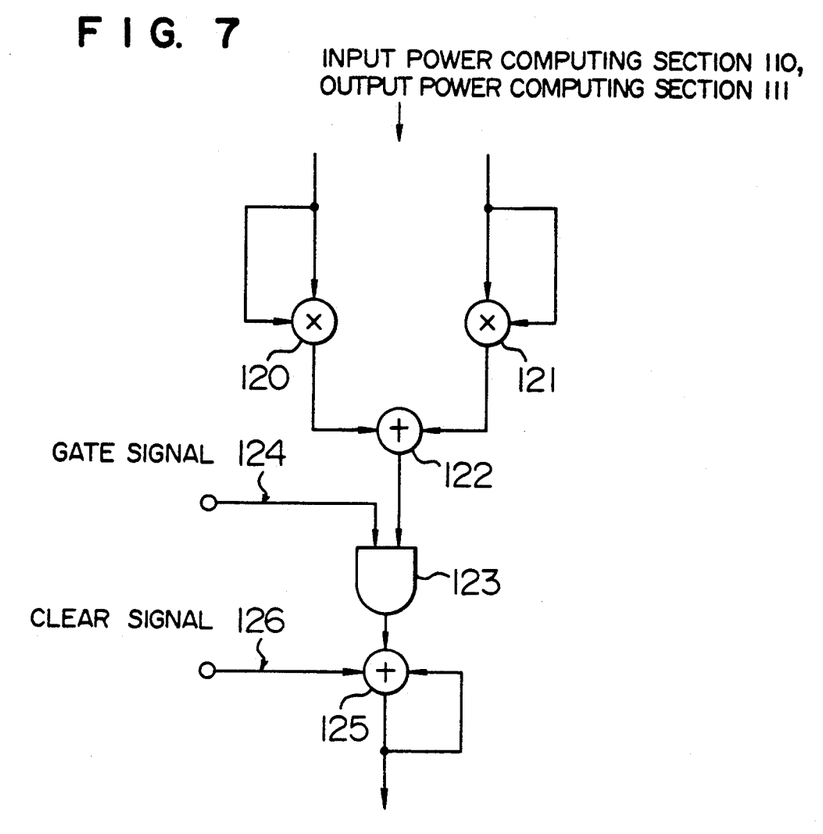
FIG. 7 is a block diagram showing in detail the structure of each of the power computing sections in the embodiment shown in FIG. 6.

FIG. 7 shows in detail the structure of an example of each of the input power computing section 110 and the output power computing section 111. Referring to FIG. 7, a combination of two squares 120 and 121, each of which multiplies two same input signals thereto by each other, and an adder 122 operates to compute a sum of the square of each of the two input signals. Then, in each period in which a gate signal 124 has high level, a computed sum outputted from the adder 122 is supplied through an AND gate 123 to an accumulator 125 so as to be cumulatively added to a value stored already in the accumulator 125. The accumulator 125 is cleared or reset, that is, is set to zero in response to application of a clear signal 126 thereto from the outside. The gate signal 124 takes high level while the ultrasonic scanning is being made in a blood flow detecting region. The clear signal 126 takes high level in synchronism with a frame synchronization signal used in the ultrasonic scanning.

Figure 8:
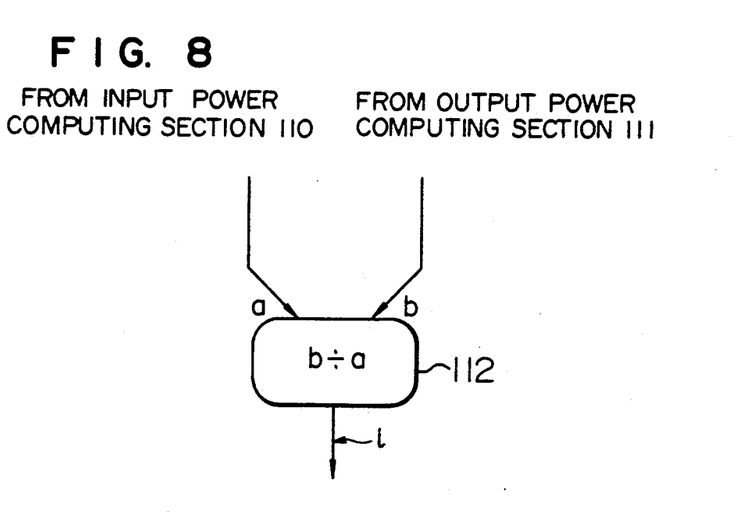
FIG. 8 is a block diagram showing in detail the structure of the comparing section in the embodiment shown in FIG. 6.

FIG. 8 shows the structure of an example of the comparing section 112. Referring to FIG. 8, the comparing section 112 performs division of an output signal b of the output power computing section 111 by an output signal a of the input power computing section 110.

Figure 9:
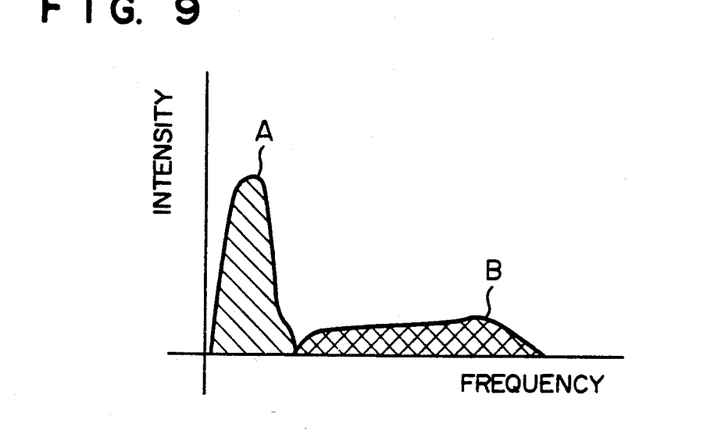
FIG. 9 illustrates the frequency distribution of an input signal applied to the MTI filter in the embodiment shown in FIG. 6.
Figure 10:
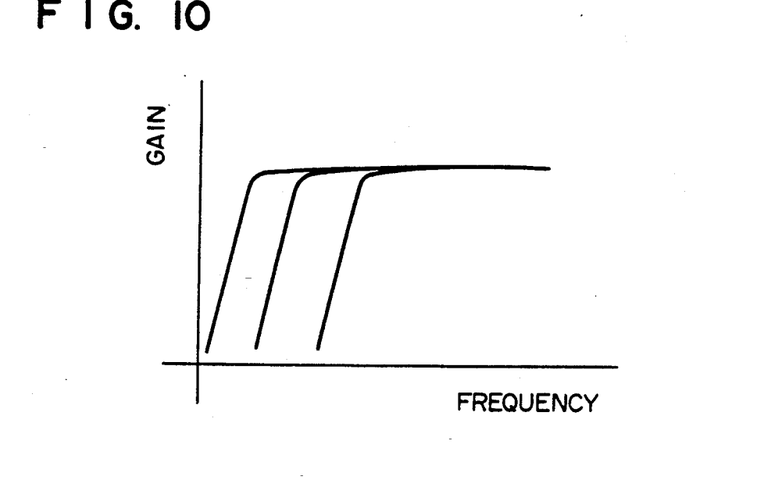
FIG. 10 shows the frequency characteristic of the MTI filter in the embodiment shown in FIG. 6.
Figure 11:
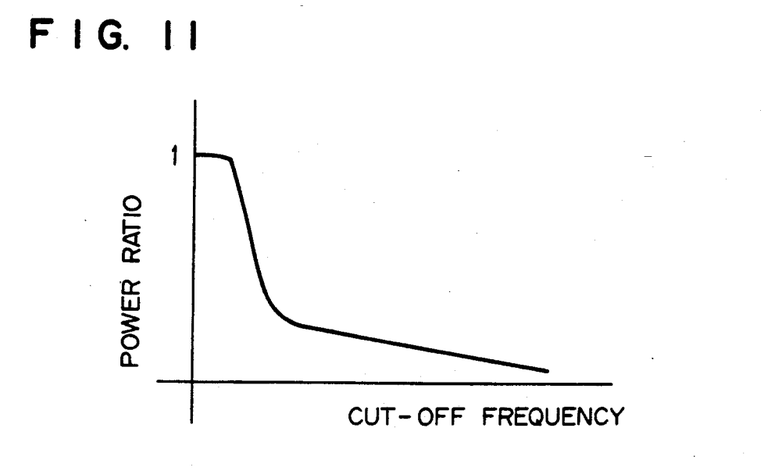
FIG. 11 shows the relation between the cut-off frequency of the MTI filter and a ratio between a power of an output signal from the MTI filter and a power of an input signal to the MTI filter in the embodiment shown in FIG. 6.

A method of controlling a filter coefficient by the coefficient control section 114 will now be described in detail. FIG. 9 is a graph illustrating the frequency distribution of the input signal to the MTI filter 105, which shows that the clutter signal and the blood flow signal coexist together in the input signal to the MTI filter 105. In FIG. 9, the frequency range A is a frequency range of the clutter signal, and the frequency range B is a frequency range of the blood flow signal. FIG. 10 shows the cut-off frequency characteristic of the MTI filter 105. When the signal shown in FIG. 9 is made to pass through the MTI filter 105 having the cut-off frequency characteristic shown in FIG. 10, the relation between a ratio of a power of the input signal to a power of the output signal of the MTI filter 105 and the cut-off frequency of the MTI filter 105 becomes as shown in FIG. 11. This relation is generally represented by a monotone decreasing function.

Figure 12:
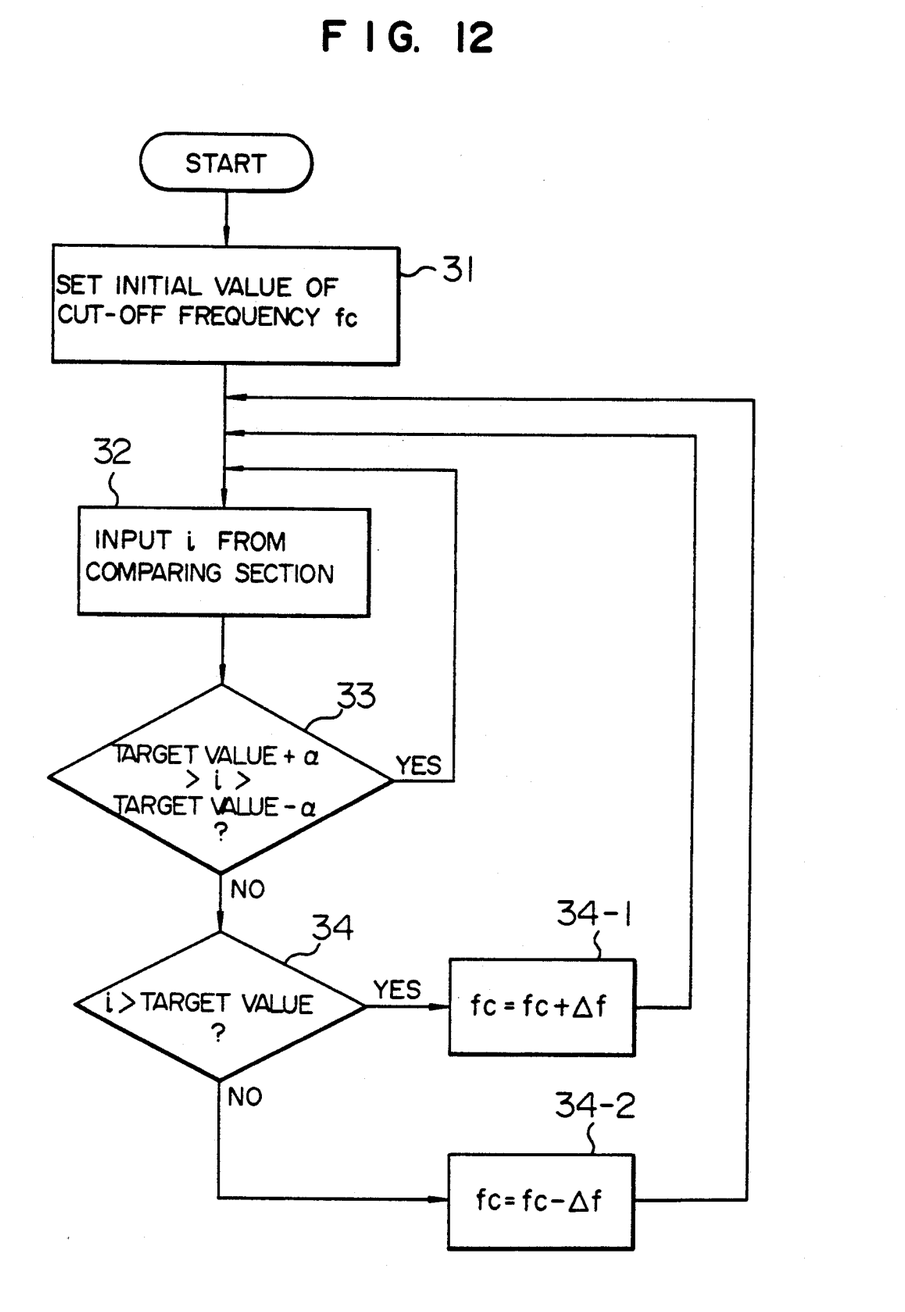
FIG. 12 is a flow chart showing the sequence of control by the coefficient control section in the embodiment shown in FIG. 6.

On the basis of such a relation between the ratio of a power of the input signal to a power of the output signal of the MTI filter 105 and the cut-off frequency of the MTI filter 105, the coefficient control section 114 controls a coefficient of the MTI filter 105 in accordance with a flow chart shown in FIG. 12.

First, in step 31, the cut-off frequency fc of the MTI filter 105 is set to its initial value. Then, in step 32, the output signal i of the comparing section 112 is applied to the coefficient control section 114 in synchronism with the application timing of the frame synchronization signal of the ultrasonic scanning. Then, in step 33, a decision is made as to whether or not the value of the input signal i from the comparating section 112 falls within a predetermined range (within $\pm \alpha$) around the target value set by the target value generating section 113. If the result of decision proves that the value of the input signal i falls within the predetermined range (within $\pm \alpha$), the processing returns to step 32. On the other hand, if the result of decision proves that, the value of the input signal i does not fall within the predetermined range (within $\pm \alpha$), a decision is made in step 34 as to whether or not the value of the input signal i from the comparing section 112 is greater than the target value. If the result of decision proves that the value of the input signal i is greater than the target value, the cut-off frequency of the MTI filter 105 is selected to be higher than the present set value in step 34-1, and the processing returns to step 32. On the other hand, if the result of decision proves that the value of the input signal i is smaller than the target value, the cut-off frequency of the MTI filter 105 is selected to be lower than the present set value in step 34-2, and the processing returns to step 32.

Figure 13:
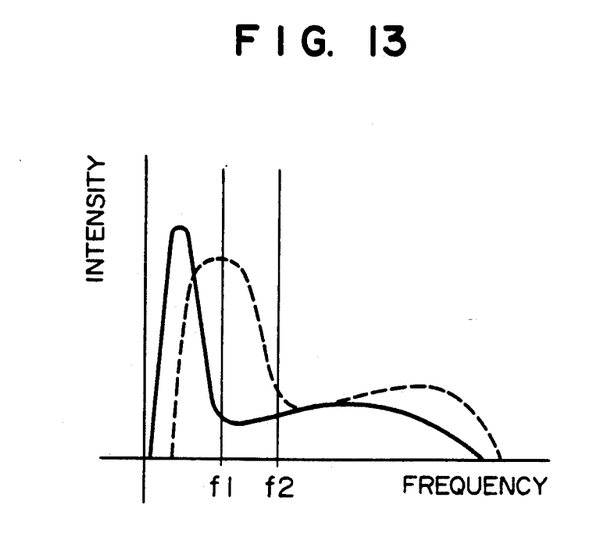
FIG. 13 shows the frequency distribution of two kinds of input signals applied to the MTI filter in the embodiment shown in FIG. 6.
Figure 14:
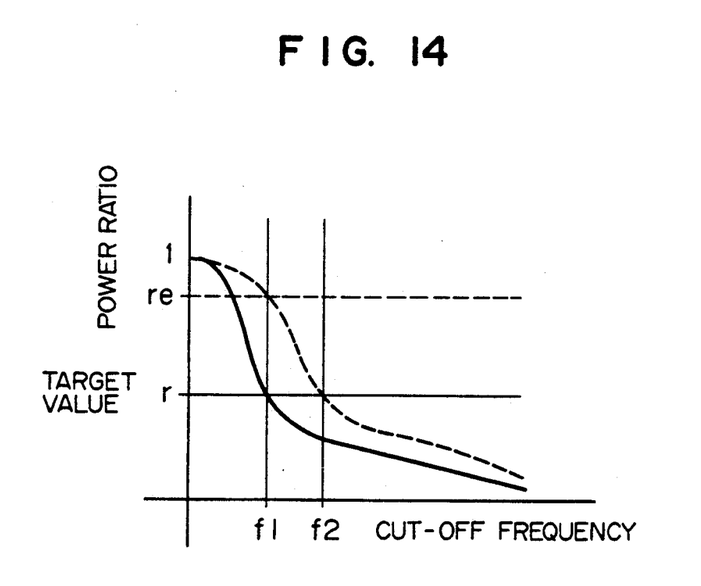
FIG. 14 shows the relation between the cut-off frequency of the MTI filter and a power ratio of an output signal and an input signal from and to the MTI filter, respectively, corresponding to the frequency distribution shown in FIG. 13.

The relation between the control of the cutoff frequency of the MTI filter 105 and a change of the intensity of the clutter signal will be explained hereunder. FIG. 13 corresponding to FIG. 9 shows the frequency distribution of the input signal to the MTI filter 105. Suppose now that the input signal has the frequency distribution indicated by the solid curve. FIG. 14 corresponding to FIG. 11 shows the relation between a ratio of a power of the input signal to a power of the output signal of the MTI filter 105 and the cut-off frequency of the MTI filter 105. Suppose also that r indicates the target value of the ratio between a power of the input signal and a power of the output signal of the MTI filter 105. In this case, the cut-off frequency of the MTI filter 105 is indicated by fl in FIG. 14. Now, when the frequency distribution of the input signal to the MTI filter 105 changes to that indicated by the dotted curve in FIG. 13, the relation between the input and output power ratio of the MTI filter 105 and the cut-off frequency of the MTI filter 105 changes also as shown by the dotted curve in FIG. 14. As a result, the output of the comparing section 112 causes the input and output power ratio of the MTI filter 105 to have a value re greater than the previous set value r. Therefore, the coefficient control section 114 operates to increase the cut-off frequency of the MTI filter 105 to a value greater than the value fl, and finally the cut-off frequency of the MTI filter 105 is increased up to a value f2. It will thus be apparent from FIG. 13 that the cut-off frequency of the MTI filter 105 is controlled in response to the intensity of the clutter signal.

Thus, according to the second embodiment described above, the rate of clutter elimination by the MTI filter 105 is always maintained constant by virtue of the function of the coefficient control section 114. As a result, it is not necessary for the operator to adjust the cut-off frequency of the MTI filter 105 in response to a change of the intensity of the clutter signal.

We claim:

1. An ultrasonic Doppler imaging apparatus comprising:
   ultrasonic pulse transmitting and receiving means for transmitting an ultrasonic pulse signal into a body under test and outputting reception signals based upon reflection of the ultrasonic pulse signal from a wave scattering portion of the body under test;
   memory means for storing the reception signals upon inputting of the reception signals thereto;
   amplitude evaluating means for evaluating an amplitude of a group of the reception signals originated from a common depth of the body under test by reading out the reception signals stored in said memory means;
   high-pass filter means, to which an output signal is applied from said amplitude evaluating means, for high-pass filtering the output signal;
   control means for controlling said high-pass filter means so as to increase a cut-off frequency of said high-pass filter means, thereby eliminating low-frequency clutter components when a result of evaluation by said amplitude evaluating means proves that many clutter components are contained in the reception signals; and
   velocity computing means for computing the moving velocity of the scattering portion of the body under test on the basis of a filtered output signal of said high-pass filter means.

2. An ultrasonic Doppler imaging apparatus according to claim 1, further comprising low-frequency component eliminating means for eliminating clutter components having very low frequencies arranged in cooperation with said amplitude evaluating means.

3. An ultrasonic Doppler imaging apparatus according to claim 1, wherein said high-pass filter means has a fixed delay time and comprises signal passing means so that, when a clutter intensity is low, the reception signal is prevented from passing through said high-pass filter means, and said velocity computing means directly obtains the moving velocity of the scattering portion of the body under test.

4. An ultrasonic Doppler imaging apparatus comprising:
   ultrasonic pulse transmitting and receiving means for transmitting an ultrasonic pulse signal into a body under test and outputting reception signals based upon reflection of the ultrasonic pulse signal from a wave scattering portion of the body under test;
   memory means for storing the reception signals upon inputting of the reception signals thereto;
   amplitude evaluating means for evaluating an amplitude of a group of the reception signals originated from a common depth of the body under test by reading out the reception signals stored in said memory means;
   high-pass filter means, to which an output signal is applied from said amplitude evaluating means, for high-pass filtering the output signal;
   low-frequency component eliminating means, provided in said amplitude evaluating means, for eliminating clutter components having very low frequencies;
   control means for controlling said high-pass filter means so as to increase a cut-off frequency of said high-pass filter means, thereby eliminating low-frequency clutter components when a result of evaluation by said amplitude evaluating means proves that many clutter components are contained in the reception signals; and
   velocity computing means for computing the moving velocity of the scattering portion of the body under test on the basis of a filtered output signal of said high-pass filter means;
   wherein said high-pass filter means has a fixed delay time and comprises signal passing means so that, when a clutter intensity is low, the reception signals are prevented from passing through said high-pass filter means, and said velocity computing means directly obtains the moving velocity of the scattering portion of said body under test.

5. An ultrasonic Doppler blood flow meter comprising:
   means for transmitting an ultrasonic pulse signal into a living body and receiving an echo signal from a reflecting portion of the living body;
   phase detecting means for subjecting the received echo signal to phase detection;
   MTI filter means for eliminating a low frequency signal from a phase detection output signal;
   power computing means for computing a power of an input signal to said filter means and a power of an output signal from said filter means;
   power comparing means for comparing said two powers with each other, thereby generating a comparison output signal;
   target value setting means for setting a target value for the low frequency signal to be eliminated by said filter means;
   control means receiving the comparison output signal of said power comparing means for controlling a filter characteristic of said filter means until the filter characteristic meets the target value set by said target value setting means; and
   velocity computing means for computing the moving velocity of the reflecting portion of the living body.

6. An ultrasonic Doppler blood flow meter according to claim 5, wherein said target value setting means permits setting of the target value by manipulating a control panel.

* * * * *